(12) United States Patent
Kwon et al.

(10) Patent No.: US 8,323,622 B2
(45) Date of Patent: Dec. 4, 2012

(54) IONIC COMPLEX NANOPARTICLES FOR DETECTING HEPARANASE ACTIVITIES AND METHOD FOR PREPARING THE SAME

(75) Inventors: Ick-Chan Kwon, Seoul (KR);
Kwang-Meyung Kim, Seoul (KR);
Kui-Won Choi, Seoul (KR);
Kyeong-Soon Park, Jeollanam-do (KR);
Seul-Ki Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 585 days.

(21) Appl. No.: 12/472,405

(22) Filed: May 27, 2009

(65) Prior Publication Data
US 2010/0233085 A1    Sep. 16, 2010

(30) Foreign Application Priority Data

Mar. 10, 2009 (KR) .................. 10-2009-0020303

(51) Int. Cl.
*A61B 5/00* (2006.01)
(52) U.S. Cl. ........................................ 424/9.6
(58) Field of Classification Search .................. None
See application file for complete search history.

(56) References Cited

OTHER PUBLICATIONS

Na et al., "Heparin/poly(l-lysine) nanoparticle-coated polymeric microspheres for stem-cell therapy", Journal of the American Chemical Society, May 9, 2007, vol. 129, No. 18, pp. 5788-5789, XP002537875, issn: 0002-7863.

Park et al., "PLGA microsphere construct coated with TGF-beta 3 loaded nanoparticles for neocartilage formation", Biomacromolecules, Aug. 2008, vol. 9, No. 8, pp. 2162-2169, XP002537876, ISSN: 1526-4602.
Johansson et al., "Intramolecular dimers: a new strategy to fluroscence quenching in dual-labeled oligonucleotide probes", Journal of the American Chemical Society, Jun. 19, 2002, vol. 124, No. 24, pp. 6950-6956, XP002537877.
Kim et al., "Cell-permeable and biocapatible polymeric nanoparticles for apoptosis imaging", Journal of the American Chemical Society, Mary 22, 2006, vol. 128, No. 11, pp. 3490-3491.
Kim et al., "Polymeric nanoparticles for protein kinase activity", Chemical Communications (Cambridge, England) Apr. 7, 2007, No. 13, pp. 1346-1348, XP002537879, ISSN: 1359-7345.

*Primary Examiner* — Paul Dickinson
(74) *Attorney, Agent, or Firm* — Fish & Richardson P.C.

(57) ABSTRACT

Disclosed are Ionic complex nanoparticles for detecting heparanase activities and a method for preparing the same. More specifically, disclosed are Ionic complex nanoparticles for detecting heparanase activities, wherein negative-ion substrate polymers specifically degraded by heparanase and positive-ion biocompatible polymers ionically bind to each other, and fluorophores or quenchers bind to each of the polymers. The ionic complex nanoparticles for detecting heparanase activities may be applied to a method for screening novel drugs such as inhibitors that prevent over-expression of heparanase. Various cells and tissues where over-expression of heparanase occurs may be non-invasively imaged in cancer cells, cancer tissues, and tissues of various inflammatory diseases. Accordingly, the ionic complex nanoparticles for detecting heparanase activities may be effectively used to early diagnose various diseases and incurable diseases including autoimmune diseases such as cancers, osteoarthritis, rheumatoid arthritis, and dementia.

21 Claims, 5 Drawing Sheets

IONIC COMPLEX NANOPARTICLES FOR DETECTING HEPARANASE ACTIVITIES AND METHOD FOR PREPARING THE SAME

RELATED APPLICATION

The present disclosure relates to subject matter contained in priority Korean Application No. 10-2009-0020303, filed on Mar. 10, 2009, which is herein expressly incorporated by reference in its entirety.

BACKGROUND OF THE INVENTION

1. Field of the Invention

The present invention relates to ionic complex nanoparticles, and particularly, to ionic complex nanoparticles for detecting heparanase activities and a method for preparing the same.

2. Background of the Invention

An extracellular matrix (ECM) serves to fill extracellular spaces of each organ and tissue, and constitutes a complex network of macromolecules for cells inside each organ. The main components of a basement membrane include collagen (type IV collagen), laminin, and heparan sulfate proteoglycan (HSPG). The HSPG is present on cell surfaces as well as in the ECM. And, the HSPG is composed of proteoglycan (core-protein+glycosaminoglycan), and heparan sulfate (HS). The HSPG has a repetitive structure of disaccharide of N-acetyl-glucosamine and glucuronic acid. HS chains fill a main space of the basement membrane. The HS may bind to a variety of proteins or growth factors, and regulate functions of the proteins. And, the HS may serve as intracellular signaling pathways between growth factors and growth factor receptors.

Cells which are invading metastatic cancer cells or leukocytes or tissues of various inflammatory diseases pass through barriers of the extracellular matrix and the basement membrane with secreting protease. Here, the protease mainly belongs to a group consisting of matrix metalloprotease (MMP), serine, cysteine and aspartic protease, and serves to degrade the ECM. The heparanase is an endoglycosidase that specifically degrades the heparan sulfate, and is a degradation enzyme that plays an important role in invasions, metastases, and growths of cells. The heparanase plays a key role in invasion to cells, and also has biological activities such as angiogenesis by dissociating HS-growth factors from the ECM.

According to the recent researches, it was newly found that a degradation enzyme such as protease and heparanase plays an important role to cause various human disease such as cancers and dementia. Various recent research has reported that matrix metalloprotease (MMP) and heparanase serve to degrade the extracellular matrix in cells and in vivo, and are related to a cell mobility due to degradation of a pericellular matrix. And, it was investigated that the degradation enzymes play an important role in cancer growths such as angiogenesis, invasion of cancer cells and metastasis. Accordingly, there have been efforts among mega pharmaceutical companies to develop novel drugs with targeting the protease and heparanase.

The heparanase plays an important role in tumor cell invasion, metastasis, and various inflammatory diseases such as rheumatoid arthritis. However, due to the lack of research on a method for imaging and analyzing activities and expressions of the heparanase, or a method for non-invasively imaging an expressed degree of the heparanase in vivo, the related technologies are required.

The conventional methods for detecting the heparanase include 2D (two-dimensional) gel methods, multi-dimensional liquid chromatography methods. However, these methods require multi-step for measuring protocols, resulting in inefficiencies in the economic and time aspects when screening plenty of drugs in the process of developing novel drugs. For detection of heparanase activities, it has been developed a sensor using polymers and XL665-streptavidin conjugate, wherein the polymers are formed by binding Europium cryptate and Biotin to HSPG (see: K. Enomoto, H. Okamoto, Y Numata, H. Takemoto, J. Pharm. Biomed, Anal, 2006, 41m 912-917). This sensor has been used as a kit for detecting heparanase activities. However, it is difficult to detect the heparanase activities expressed in cells and in vivo, or to early diagnose diseases by using the sensor.

SUMMARY OF THE INVENTION

Therefore, an object of the present invention is to provide an ionic complex nanoparticle for detecting heparanase activities expressed in cells and in vivo, and a method for preparing the same.

Another object of the present invention is to provide a composition for diagnosing cancers, strokes, and autoimmune diseases, or a composition for a quantitative analysis of heparanase, in which compositions comprise the ionic complex nanoparicle disclosed in the present invention.

According to a first aspect, to achieve these and other advantages and in accordance with the purpose of the present invention, as embodied and broadly described herein, there is provided ionic complex nanoparticles for detecting heparanase activities, in which negative-ion substrate polymers specifically degraded by heparanase and positive-ion biocompatible polymers ionically bind to each other, and fluorophores and quenchers bind to each of the polymers.

In one embodiment of the present invention, the nanoparticle of the present invention may be an ionic complex nanoparticle for detecting heparanase activities, which is represented by the following chemical formula 1.

[Chemical Formula 1]

Here, 'A' indicates the fluorophore, 'B' indicates the negative-ion substrate polymer specifically degraded by heparanase, 'C' indicates the quencher to implement a quenching effect by absorbing fluorescence emitted from the fluorophore, and 'D' indicates the positive-ion biocompatible polymer that can be specifically accumulated on tissues of cancers and inflammatory disease. Here, positions of 'A' and 'C' may be interchangeable with each other, and positions of 'B' and 'D' may be interchangeable with each other. The 'B' and 'D' bind ionically to each other. In the chemical formula 1, the solid line indicates a chemical binding such as a covalent binding, and the dotted line indicates an ionic-binding.

According to a second aspect, the present invention provides a contrast agent composition for imaging heparanase expressed in cells and tissues, the composition comprising the ionic complex nanoparticles for detecting heparanase activities.

In one embodiment of the present invention, the fluorophore may be selected from a group consisting of fluorescein, BODIPY, Tetramethylrhodamine, Alexa, Cyanine, allopicocyanine fluorophores and derivatives thereof.

In another embodiment of the present invention, the fluorophore may be Cyanine or Alexa fluorophores that emit fluorescence of red or infrared rays.

In still another embodiment of the present invention, the quencher may be selected from a group consisting of a blackhole quencher (BHQ), a blackberry quencher (BBQ), and derivatives thereof.

In still another one embodiment of the present invention, the negative-ion substrate polymer specifically degraded by heparanase may be selected from a group consisting of heparan sulfate (HS), heparan sulfate proteoglycans (HSPG), heparin, chondroitin-4-sulfate (C4S), chondroitin-6-sulfate (C6S), dermatan sulfate (DS), keratan sulfate (KS) and hyaluronic acid (HA).

In still another embodiment of the present invention, the positive-ion biocompatible polymer is the polymer that form ionic-complex nanoparticle, by an electrostatic attractive force, together with the negative-ion substrate polymer specifically degraded by heparanase. This positive-ion biocompatible polymer may be selected from a group consisting of glycol chitosan, chitosan, poly-L-lysine (PLL), poly beta-amino ester polymer, polyethylenimine (PEI), poly (amidoamine) (PAMAM) dendrimer, and derivatives thereof.

In still another embodiment of the present invention, the negative-ion substrate polymer or the positive-ion biocompatible polymer may have molecular weight of 2,000-500,000 Da.

In still another embodiment of the present invention, 1-30 mol of the fluorophore or the quencher may bind to 1 mol of the negative-ion substrate polymer or the positive-ion biocompatible polymer. In case the fluorophore or quencher is out of the above range, the polymers may have transformed characteristics such as structure changes or charge changes, resulting in lowered fluorescence or quenching effects, thusly the above range is preferable.

In still another embodiment of the present invention, the fluorophore may bind to the negative-ion substrate polymers, and the quencher may bind to the positive-ion biocompatible polymers.

In still another embodiment of the present invention, the fluorophores-bound negative-ion substrate polymer and the quenchers-bound positive-ion biocompatible polymer may bind to each other with a ratio therebetween within the range of 1:0.1-1:10. Here, the negative-ion substrate polymer and the positive-ion polymer bind to each other by an electrostatic attractive force. The ratio between the negative-ion substrate polymer and the positive-ion polymer may be varied according to the kinds of used polymers. However, when the negative-ion substrate polymer and the positive-ion polymer bind to each other with a ratio rather than the above ratio, a substantial binding may not occur, thusly the above range is preferable.

In still another embodiment of the present invention, the ionic-complex nanoparticle may have sizes of 50-800 nm.

In still another embodiment of the present invention, a distance between the fluorophore and the quencher inside the ionic-complex nanoparticle may be 20 nm or less.

According to a third aspect, the present invention provides a composition for a quantitative analysis of heparanase enzymes expressed in cells and tissues, wherein the composition comprises the ionic-complex nanoparticle for detecting heparanase activities as effective components.

According to a fourth aspect, the present invention provides a composition for screening drugs or effects of drugs, the drugs capable of preventing over-expression of the heparanase in cells and tissues, wherein the composition comprises the ionic-complex nanoparticle for detecting heparanase activities as effective components.

According to a fifth aspect, the present invention provides a method for imaging heparanase for providing information necessary to diagnose cancers, osteoarthritis, rheumatoid arthritis, progressive systemic sclerosis, chronic thyroiditis, ulcerative colitis, or multiple sclerosis by using the ionic-complex the ionic complex nanoparticle.

In one embodiment of the present invention, the cancers may be selected from a group consisting of squamous cell carcinoma, uterine carcinoma, uterine cervical cancer, prostatic carcinoma, head and neck caner, pancreatic carcinoma, brain tumor, breast cancer, liver cancer, skin cancer, esophageal cancer, testicular carcinoma, kidney cancer, large intestine cancer, rectal cancer, stomach cancer, bladder cancer, ovarian cancer, cholangio carcinoma, and gallbladder carcinoma.

According to a sixth aspect, the present invention provides a method for preparing ionic complex nanoparticles for detecting heparanase activities, wherein the method comprises:

binding fluorophores to negative-ion substrate polymers specifically degraded by heparanase, and binding quenchers to positive-ion biocompatible polymers; and ionically binding the fluorophores-bound negative-ion substrate polymer, to the quenchers-bound positive-ion biocompatible polymers, thereby forming ionic-complex nanoparticles.

The present invention has the following effects.

As discussed above, the ionic complex nanoparticle for detecting heparanase activities is in a non-fluorescent state due to a high quenching effect with respect to fluorescent materials, but emits strong fluorescence only when substrate polymers are degraded by heparanase. Accordingly, the ionic complex nanoparticle for detecting heparanase activities may be applied to a method for screening novel drugs such as inhibitors that prevent over-expression of heparanase.

Furthermore, various cells and tissues where over-expression of heparanase occurs can be non-invasively imaged in cancer cells, cancer tissues, and tissues of various inflammatory diseases. Accordingly, the ionic complex nanoparticle for detecting heparanase activities can be effectively used to early diagnose various diseases and incurable diseases including autoimmune diseases, cancers, osteoarthritis, rheumatoid arthritis, and dementia.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE INVENTION

Description will now be given in detail of the present invention, with reference to the accompanying drawings.

Where the plural form is used for compounds, materials, diseases, and the like, this is intended to mean one (preferred) or more single compound(s), material(s), disease(s), or the like, where the singular or the indefinite article ("a", "an") is used, this is intended to include the plural or preferably the singular.

In order to solve the aforementioned problems, the present invention provides ionic complex nanoparticles for detecting heparanase activities, and a method for preparing the same capable of real-time and non-invasively imaging heparanase in vivo at the molecular level.

More particularly, the present invention is to provide ionic complex nanoparticles for detecting heparanase activities expressed in cells and in vivo, and a method for preparing the same, wherein the nanoparticles are formed by binding n egative-ion substrate polymers bound to fluorophores, to positive-ion polymers bound to quenchers by an electrostatic attractive force. Especially, the present invention relates to nanoparticles specifically reacting with heparanase, and implementing a fluorescent characteristic only on a specific heparanase target, and a contrast agent composition for disease diagnosis.

Figure 1:
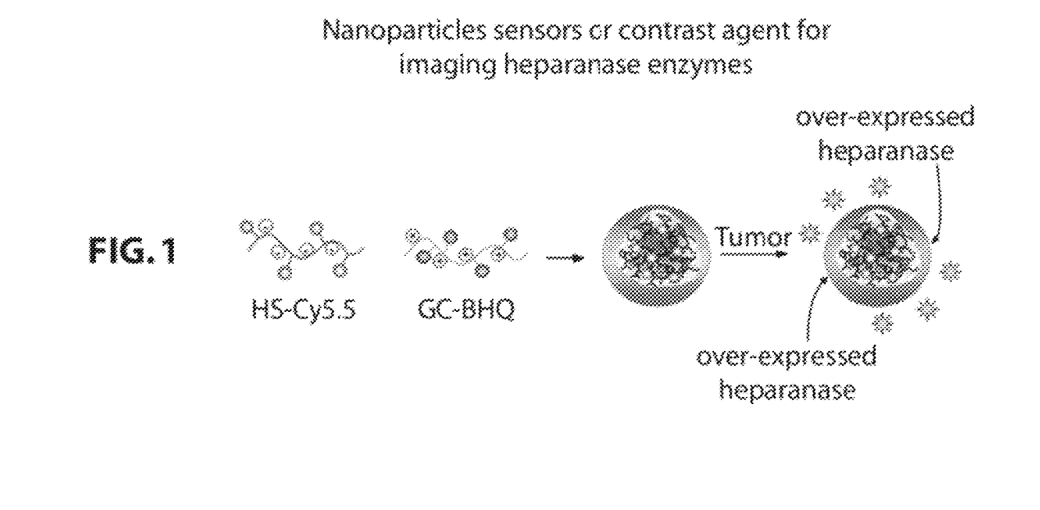
FIG. 1 shows an ionic-complex nanoparticle formed as fluorophore-bound negative-ion substrate polymer bind to quencher-bound positive-ion biocompatible polymer, in which the substrate polymer is degraded by heparanase thus to restore a fluorescent state.

When no heparanases are present, the nanoparticles according to the present invention, i.e., nanoparicles formed by positive-ion biocompatible polymers to which quenchers are chemically bound, and negative-ion substrate polymers which are heparanase substrates to which fluorophores are chemically bound, are have a quenching effect. Such quenching effect arises from absorbing fluorescence emitted from the fluorophore by the quencher. However, as shown in FIG. 1, when heparanases are present, the heparanase substrate polymers inside the nanoparticles react with the heparanase enzymes thus to be degraded. As a result, the fluorophores and the quenchers are separated from each other thus to be spacing from each other, thereby causing a quenching effect to disappear. Accordingly, the fluorophores emit their own fluorescence, thereby allowing the heparanase enzymes to be analyzed in qualitative and quantitative manners. The ionic complex nanoparticles for detecting heparanase activities of the present invention can serve to rapidly screen heparanase activities and inhibition of activities through an imaging process, and enable real-time cell imaging and non-invasive tissue imaging in cells and in vivo.

More particularly, the present invention relates to a sensor for imaging heparanase enzymes expressed in cells or in vivo, which is represented by the following chemical formula 1.

[Chemical Formula 1]

$$A\text{-}B^{\ominus}$$
$$\vdots$$
$$C\text{-}D^{\oplus}$$

Here, 'A' indicates the fluorophore, 'B' indicates the negative-ion substrate polymer specifically degraded by heparanase, 'C' indicates the quencher to implement a quenching effect by absorbing fluorescence emitted from the fluorophore, and 'D' indicates the positive-ion biocompatible polymer. Here, positions of 'A' and 'C' may be interchangeable with each other, and positions of 'B' and 'D' may be interchangeable with each other. The $\ominus$ and $\oplus$ indicate negative ions and positive ions, respectively. And, the $B^{\ominus}$ and $D^{\oplus}$ ionically bind to each other.

The fluorophore 'A' or the quencher 'C' chemically bind to the negative-ion substrate polymer (B), or to the positive-ion biocompatible polymer (D).

In the chemical formula 1, the solid line indicates a chemical binding such as a covalent binding, and the dotted line indicates an ionic-binding.

As used herein, the "fluorophore(s)" indicates the fluorophore(s) binds to the polymer corresponding to substrate of heparanase enzyme, and includes fluorescein, BODIPY (Invitrogen Co.), T etramethylrhodamine, Alexa (Molecular Probes® Product), Cyanine, allopicocyanine, other fluorophores that emit fluorescence, or derivatives thereof. Available fluorophores may include fluorophores disclosed in Tavi's "FluoroTable": Common fluorophores (from Zeiss Corporation web site and http://info.med.yale.edu/genetics/ward/tavi/FISHdyes2.html), and the thesis is referred and integrated in the present specification in its entirety.

As the fluorophores, fluorophores that emit fluorescence of red or infrared rays, and have a high quantum yield are preferred. Among the fluorophores discussed above, the Cyanine and Alexa fluorophores are especially preferred, because they emit and absorb near infrared rays thus to minimize interference with cells or absorption into cells, bloods, and living tissues, etc.

As used herein, the "negative-ion substrate polymer(s) specifically degraded by heparanase" may include heparan sulfate (HS), heparan sulfate proteoglycans (HSPG), heparin, chondroitin-4-sulfate (C4S), chondroitin-6-sulfate (C6S), dermatan sulfate (DS), keratan sulfate (KS) and hyaluronic acid (HA).

The quencher implement a high quenching effect by absorbing wavelength of fluorescence emitted from fluorophore chemically bound to the negative-ion substrate polymer (negative-ion peptide substrate polymer). Accordingly, when the peptide substrate polymer is not degraded by heparanase enzymes, the fluorescence is not emitted. This quenching effect is implemented when a distance between the fluorophore and the quencher is within several tens of nanometers. That is, if peptide substrate polymer is degraded by heparanase enzyme, the fluorophore and the quencher bound to the peptide are separated from each other thus to be spacing from each other, thereby causing the quenching effect to disappear. Accordingly, the fluorophore emits its own fluorescence, thereby enabling qualitative and quantitative analysis of heparanase enzyme.

The types of fluorophores to be used are depend on ranges of wavelength of fluorescence emitted from the fluorophores. The quenching effect can be maximized only when using quenchers having the same or almost similar wavelength as or to that of fluorescence emitted from fluorophores. The quenchers used in the present invention are 'dark quenchers' capable of quenching fluorescence of the fluorophores not by emitting out absorbed excited fluorescence energy. The commercially available quenchers may include Black Hole Quencher™ Dyes, product from Biosearch Technologies Inc. (BHQ), BlackBerry™ Quencher 650, product from BERRY&ASSOCIATES Inc. (BBQ), derivatives thereof, etc.

Pairs of fluorophores and quenchers that can be used in the present invention are shown in the following table 1.

patible polymers with a mixture ratio of 1:0.1-1:10. Preferably, the formed nanoparticles have sizes of 50-800 nm.

As used herein, the "mixture ratio" between the fluorophores-negative ion substrate polymers and the quenchers-positive ion biocompatible polymers indicates an optimum ratio for binding the two polymers to each other. For instance, when an amount of the quenchers-positive ion biocompatible polymers is too large than the fluorophores-negative ion substrate polymers, it is not preferable because fluorescence may not be recovered due to a high concentration of the quenchers after the substrate polymers are degraded and may not achieve the purpose of the present invention, even if a quenching effect is excellent.

In the case that an in vivo experiment is performed in a cancer model so as to measure heparanase activities, preferably, nanoparticles have sizes large enough for a syringe to be easily injected into a blood vessel. If the nanoparticles have sizes of more than 1 μm, they can not be delivered to desired lesions. Accordingly, the nanoparticles preferably have sizes of 50-800 nm.

A distance between the fluorophores and the quenchers of the formed ionic-complex nanoparticles has to be controlled so as to maximize a quenching effect. Accordingly, it is pref-

TABLE 1

| | Quencher | |
| --- | --- | --- |
| Types | nm (Quenching range) | Fluorophores Types |
| BHQ-1 Amine<br>BHQ-1 Carboxylic Acid<br>BHQ-1 Carboxylic Acid, Succinimidyl Ester | 480-580 | FITC, FAM, TET, JOE, HEX, Oregon Green ®, Alexa Fluor ® 500, Alexa Fluor ® 514, Alexa Fluor ® 532, Alexa Fluor ® 546, BODIPY ® 493/503, BODIPY ® 580/550, BODIPY ® 558/568 |
| BHQ-2 Amine<br>BHQ-2 Carboxylic Acid<br>BHQ-2 Carboxylic Acid, Succinimidyl Ester | 550-650 | TAMRA, ROX, Cy3, Cy3.5, CAL Red ™, Red 640, Alexa Fluor ® 568, Alexa Fluor ® 594, Alexa Fluor ® 610, BODIPY ® 581/591 |
| BHQ-3 Amine<br>BHQ-3 Carboxylic Acid<br>BHQ-3 Carboxylic Acid, Succinimidyl Ester | 620-730 | Cy5, Cy5.5, Alexa Fluor ® 647, Alexa Fluor ® 660, Alexa Fluor ® 680, Alexa Fluor ® 700. |
| BHQ-10 Carboxylic Acid | 480-580 | FITC, FAM, TET, JOE, HEX, Oregon Green ®, Alexa Fluor ® 500, Alexa Fluor ® 514, Alexa Fluor ® 532, Alexa Fluor ® 546, BODIPY ® 493/503, BODIPY ® 530/550, BODIPY ® 558/568 |
| BBQ 650 | 530-750 | Cy3, TAMRA, Texas Red, ROX, Cy5, Cy5.5, Rhodamine, Alexa Fluor ® 568, Alexa Fluor ® 594, Alexa Fluor ® 610, Alexa Fluor ® 647, Alexa Fluor ® 660, Alexa Fluor ® 680, Alexa Fluor ® 700, BODIPY ® 493/503, BODIPY ® 530/550, BODIPY ® 558/568, BODIPY ® 581/591 |

As used herein, the "positive-ion biocompatible polymer(s)" indicates the biocompatible polymer that can form ionic-complex nanoparticles by an electrostatic attractive force together with the negative-ionic substrate polymer. For instance, the positive-ion biocompatible polymer may include glycol chitosan, chitosan, poly-L-lysine (PLL), poly beta-amino ester polymer and synthesized derivatives thereof, poly ethylenimine (PEI) and derivatives thereof, poly (amidoamine) (PAMAM), dendrimer and derivatives thereof.

The fluorophores-bound negative-ion substrate polymers are reacted with the quenchers-bound positive-ion biocompatible polymers, in an aqueous solution by an electrostatic attractive force, thereby forming ionic-complex nanoparticles. Preferably, the fluorophores-negative ion substrate polymers are mixed with the quenchers-positive ion biocomerable to maintain a distance of 20 nm or less, so as to minimize a fluorescence intensity of the fluorophores by the quenching effect.

As the negative-ion substrate polymers or positive-ion biocompatible polymers, polymers having molecular weight of 2,000-500,000 Da may be used. Preferably, 1-30 mol of the fluorophores or quenchers may chemically bind to 1 mol of the negative-ion substrate polymers or the positive-ion biocompatible polymers. As discussed above, when the fluorophores or quenchers out of the range of 1-30 mol bind to 1 mol of the negative-ion substrate polymers or the positive-ion biocompatible polymers, the polymers may have transformed characteristics such as structure changes or charge changes, thusly the above binding ratio is preferred.

In a preferred embodiment of the present invention, the negative-ion substrate polymer is heparan sulfates (HS), which is over-expressed in various inflammatory tissues such as cancers, rheumatoid arthritis, osteoarthritis, and arteriosclerosis, and which is degraded by heparanase. The fluorophore is cyanine fluorophores Cy5.5 which shows a near-infrared fluorescence by chemically binding to the substrate polymer. The positive-ion biocompatible polymer is glycol chitosan (GC) that can form nanoparticles together with the negative-ion substrate polymer by an electrostatic attractive force. And, the quencher is black hole quencher-3 (BHQ-3) capable of maximizing a quenching effect by absorbing fluorescence emitted from the fluorophore by chemically binding to the positive-ion biocompatible polymer. However, the respective substance may not limited to the above materials.

The ionic-complex nanoparticles for detecting heparanase activities according to the present invention may be prepared by mixing the fluorophores-bound negative-ion substrate polymers, with the quenchers-bound positive-ion biocompatible polymers, by an electrostatic attractive force therebetween.

More particularly, the present invention relates to a method for preparing ionic-complex nanoparticles for detecting heparanase activities, comprising: binding fluorophores to negative-ion substrate polymers specifically degraded by heparanase; and binding quenchers to positive-ion biocompatible polymers; ionically binding the fluorophpores-bound negative-ion substrate polymers, to the quenchers-bound positive-ion biocompatible polymers, thereby forming ionic-complex nanoparticles.

The fluorophores may chemically bind to not only negative-ion substrate polymers, but also positive-ion biocompatible polymers. Likewise, the quenchers may chemically bind to not only negative-ion substrate polymers, but also positive-ion biocompatible polymers.

Non-limiting examples of the chemical binding may include i) binding fluorophores or quenchers to positive-ion biocompatible polymers or negative-ion substrate polymers through a covalent binding, and ii) binding fluorophores or quenchers to positive-ion biocompatible polymers or negative-ion substrate polymers through a linker.

More specifically, when amine groups are present at the polymers, and N-hydroxysuccinimide (NHS type) groups are present at the fluorophores and the quenchers; a covalent binding can occur therebetween. Alternatively, when COOH groups are present at the polymers, and amine groups are present at the fluorophores and the quenchers; the two remaining groups cannot directly bind to each other. Accordingly, the two group are chemically bound to each other by using a cross linker (e.g., dicyclohexylcarbodiimide (DCC), 1-ethyl-3-(3-dimethylaminopropyl)-carbodiimide, hydrochloride (EDAC)).

Also, if necessary, the method may further comprise purifying or identifying the fluorophores-polymers or the quenchers-polymers. The fluorophores or quenchers may bind to the negative-ion substrate polymers or positive-ion polymers by using various techniques well-known to those skilled in the art.

The ionic-complex nanoparticles comprising of fluorophores-negative ion substrate polymers and quenchers-positive ion polymers are prepared with a minimized fluorescent state due to a quenching effect implemented as the quenchers absorb fluorescence emitted from the fluorophores. As shown in the table 1, there are various fluorophores having different wavelengths, and various quenchers corresponding thereto. Non-limiting examples of the negative-ion substrate polymers which are heparanase substrate polymers include heparan sulfate (HS), heparan sulfate proteoglycan (HSPG), heparin, chondroitin-4-sulfate (C4S), chondroitin-6-sulfate (C6S), dermatan sulfate (DS), keratan sulfate (KS), hyaluronic acid (HA). Also, non-limiting examples of the positive-ion biocompatible polymers include glycol chitosan, chitosan, poly-L-lysine (PLL), poly beta-amino ester polymer and synthesized derivatives thereof, polyethyleneimine (PEI) and derivatives thereof, poly(amidoamine) (PAMAM) dendrimer and derivatives thereof. Accordingly, various ionic-complex nanoparticles may be prepared by modifying the types of the negative-ion substrate polymers and the positive-ion polymers. That is, a various ionic-complex nanoparticles for detecting heparanase enzymes can be prepared, because the method is easy to control, and the fluorophores and the quenchers at desired wavelengths are selectable.

Since the ionic-complex nanoparticles for detecting heparanase activities can serve to easily identify whether heparanase enzymes are present on specific tissues or cells in vivo, whether heparanase enzymes are in activated state or non-activated state, etc., they can be applied to a cell imaging system, a specific tissue imaging system, a drug delivery system, etc.

A contrast agent composition comprising the nanoparticles disclosed in the present invention can be applied both in vivo and in vitro. Furthermore, the contrast agent composition can be applied to a high-throughput screening (HTS) method necessary for the development of novel drugs, and can be applied to real-time identify whether heparanase enzymes are present in vivo, to measure an activated degree, to early diagnose diseases, etc. More particularly, the contrast agent composition can be applied to a method for imaging heparanase enzymes expressed in cancers, osteoarthritis, rheumatoid arthritis, autoimmune diseases in vivo and in vitro, a method for screening effects of drugs which inhibit over-expression of heparanase enzymes.

The contrast agent composition comprising the nanoparticles disclosed in the present invention can be applied to a method for imaging heparanase enzymes expressed in cancers including squamous cell carcinoma, uterine carcinoma, uterine cervical cancer, prostatic carcinoma, head and neck cancer, pancreatic carcinoma, brain tumor, breast cancer, liver cancer, skin cancer, esophageal cancer, testicular carcinoma, kidney cancer, large intestine cancer, rectal cancer, stomach cancer, bladder cancer, ovarian cancer, cholangio carcinoma, and gallbladder carcinoma.

Further, the contrast agent composition comprising the nanoparticles disclosed in the present invention can be applied to a method for imaging heparanase enzymes expressed in intractable diseases including dementia and stroke.

EXAMPLES

Hereinafter, the ionic complex nanoparticles for detecting heparanase activities, and a method for preparing the same according to the present invention will be explained in more detail in the following preparation examples. However, the following preparation examples are merely exemplary, but do not limit the scope of the present invention.

Preparation Example 1

Method for Preparing Ionic-Complex Nanoparticles Sensor 1-1. Synthesis of Heparan Sulfate-Cy5.5 (HS-Cy5.5) and Glycolchitosan-BHQ3 (GC-BHQ3)

As one example of fluorophores-negative ion substrate polymers, HS-Cy5.5 was synthesized as shown in the following reaction formula 1. 50 mg of heparan sulfate and 9 mg of Cy5.5-NHS were dissolved in 0.1M of $NaHPO_4$ (5 ml, pH 9.0), and were reacted with each other at a room temperature for 6 hours in dark place. Next, the solution was dialyzed in distilled water for two days, and then was lyophilized. It was observed through UV that about 2 mol of Cy5.5 had bound to 1 mol of heparan sulfate.

As one example of positive ion biocompatible polymers-quenchers, glycol chitosan-BHQ3 was synthesized as shown in the following reaction formula 1. 100 mg of glycol chitosan and 11.5 mg of BHQ3-NHS were dissolved in 10 ml of DMSO, and then were reacted for 4 hours. Next, the reaction mixture was dialyzed in a co-solvent of water and methanol (1v:1v) for a day. Then, the reaction mixture was dialyzed in water for a day, and then was lyophilized. It was observed through UV that about 4 mol of the BHQ3 had bound to 1 mol of the glycol chitosan.

[Reaction Formula 1]

1. Synthesis of HS-Cy 5.5

Heparan sulfate

X = H or $SO_3^-$; Y = AC, $SO_3^-$ or H

Cy 5.5

HS-Cy 5.5

Cy 5.5

2. Synthesis of GC-BHQ 1-2. Changes of Sizes and Optical Characteristics of Ionic-Complex Nanoparticles Comprised of HS-Cy5.5 and GC-BHQ3

Tests were performed about whether HS-Cy5.5 and GC-BHQ3 form ionic-complex nanoparticles in an aqueous solution, and whether a quenching effect is obtained at the time of forming nanoparticles.

Analyzed were characteristics of prepared ionic-complex nanoparticles in a condition that HS-Cy5.5 has a fixed concentration of 0.2 mg/ml, and GC-BHQ3 has a concentration varying from 0 mg/ml to 0.6 mg/ml.

Figure 2A:
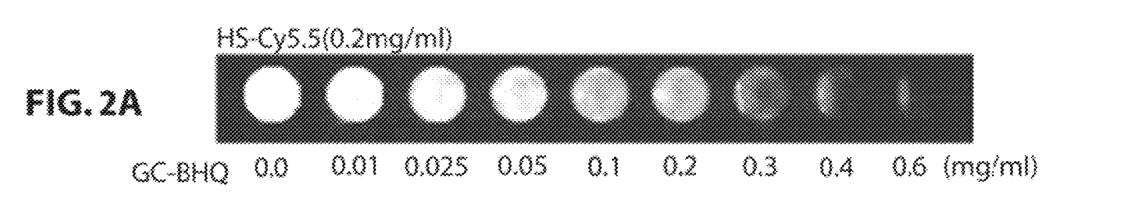
FIG. 2A shows changes of optical characteristics according to concentration ratios between heparan sulfate bound to fluorophores Cy5.5 (HS-Cy5.5) and Glycol chitosan bound to quenchers BHQ3 (GC-BHQ3)
Figure 2B:
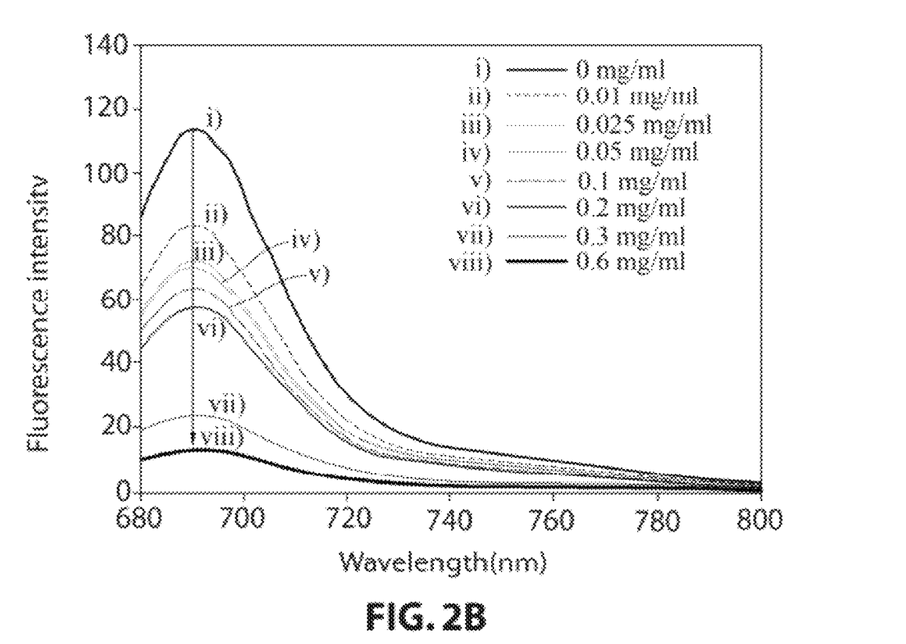
FIG. 2B shows changes of optical characteristics according to concentration ratios between the fluorophores Cy5.5-bound heparan sulfate (HS-Cy5.5) and the quenchers (BHQ3)-bound Glycol chitosan (GC-BHQ3), which were measured by a fluorescence analyzer.

As shown in FIG. 2A, nanoparticles prepared by increasing an amount of GC-BHQ3 added to HS-Cy5.5 exhibited a gradually decreased fluorescence intensity. As shown in FIG. 2B, a maximum quenching effect was implemented when a ratio between HS-Cy5.5 and GC-BHQ3 was 0.2:0.6. When compared to a fluorescence intensity of the HS-Cy5.5 only, the mixture of HS-Cy5.5 and GC-BHQ3 has a fluorescence intensity decreased by about 80% or more. From these experiments, it could be seen that the ionic-complex nanoparticles comprised of HS-Cy5.5 and GC-BHQ3 exhibited a quenching effect.

Figure 2C:
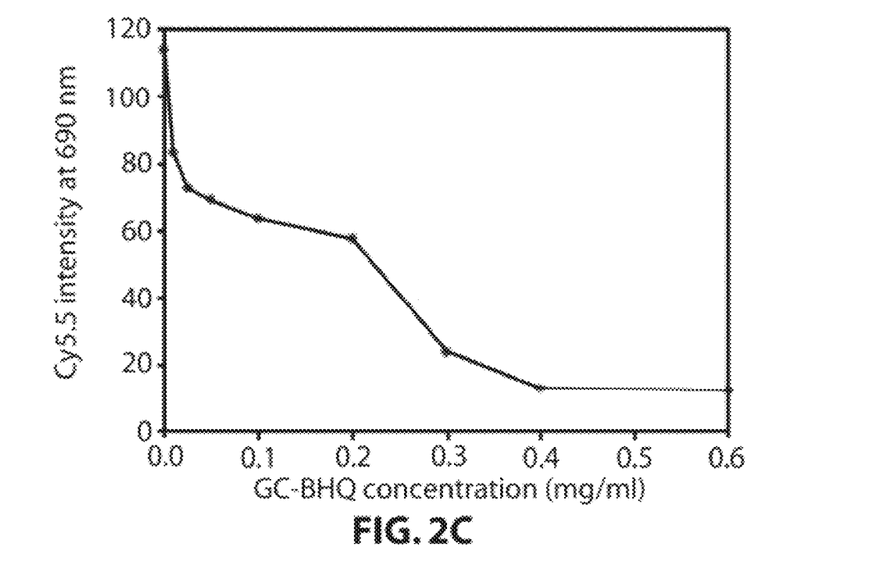
FIG. 2C shows a Cy5.5 intensity according to a GC-BHQ concentration, which represents a quenching effect of nanoparticles composed of HS-Cy5.5/GC-BHQ3.
Figure 2D:
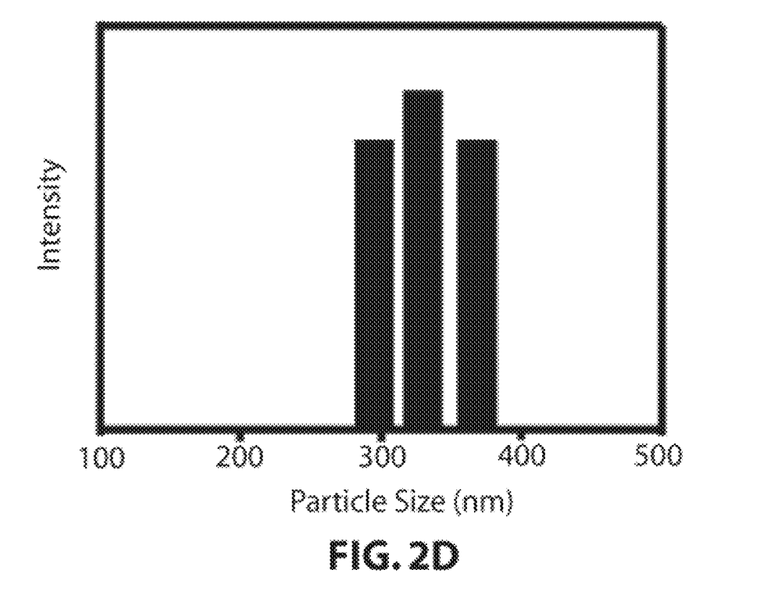
FIG. 2D shows sizes of nanoparticles formed when a ratio of HS-Cy5.5/GC-BHQ3 is 0.2:0.6.

As shown in FIG. 2C, a maximum quenching effect was obtained when a ratio between HS-Cy5.5 and GC-BHQ3 was 0.2:0.6. Under this ratio of 0.2:0.6, nanoparticles having sizes about 330 nm were formed in an aqueous state as shown in FIG. 2D.

Experimental Example 1

Tests for the Ability of Heparanase Inhibitor to Inhibit Heparanase, by Using Ionic-Complex Nanoparticles of HS-Cy5.5/GC-BHQ3

By using the ionic-complex nanoparticles of HS-Cy5.5/GC-BHQ3 prepared in the preparation example 1, heparanase activities with or without heparanase inhibitor treatment were imaged.

Figure 3:
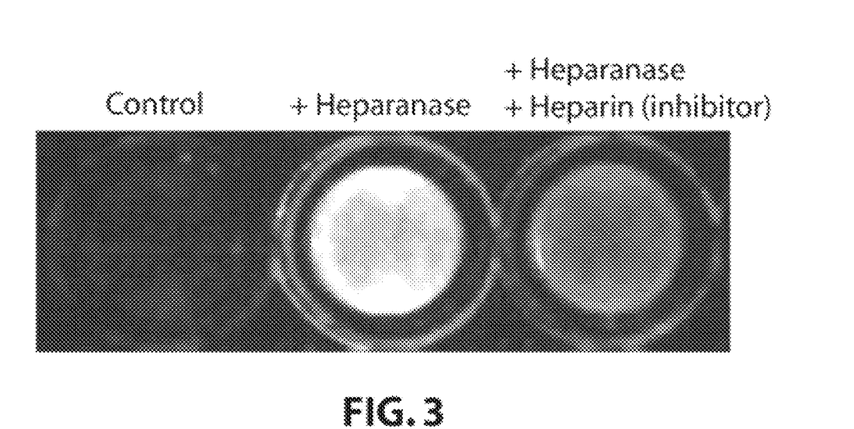
FIG. 3 shows changes of fluorescence when nanoparticles composed of HS-Cy5.5/GC-BHQ3 is simultaneously treated with 'heparanase' and 'heparanase+inbihitor'.

The ionic-complex nanoparticles of HS-Cy5.5/GC-BHQ3 prepared in the preparation example 1 were treacted with 'heparanase' and 'heparanase+inhibitor' at a temperature of 37□ for one hour, and then fluorescence emission therefrom by an enzyme degradation reaction was observed. After lapse of one hour, the fluorescence of the nanoparticles was observed by using a Kodak Image Station 4000MM Digital Imaging System mounted with a charge coupled device (CCD) camera. As a result, as shown in FIG. 3, the fluorescence intensity was increased when the heparanase was treated, whereas the fluorescence intensity was decreased when the 'heparanase+inhibitor' were treated. From the result, it could be seen that the ionic-complex nanoparticles of HS-Cy5.5/GC-BHQ3 could image heparanase enzymes, and could be applied to a composition for screening drugs of heparanase inhibitors or effects of drugs.

Experimental Example 2

Imaging of Heparanase Expression in Cancer Models Using Ionic-Complex Nanoparticles of HS-Cy5.5/GC-BHQ3

To establish a cancer model, $1 \times 10^6$ SCC7 cancer cells were implanted in nude mice. Here, the SCC7 are epithelial cancer cells, and commercially available from American Type Culture Collection (ATCC). Next, when the cancer has a size of about 5-8 mm, the ionic-complex nanoparticles of HS-Cy5.5/GC-BHQ3 were injected into veins of the mice tails. Then, heparanase expression was imaged by using an eXplore Optix image device.

It is known that the SCC7 cancer tissues express a large amount of heparanase. Accordingly, in order to test the ability of a heparanase inhibitor to inhibit heparanase, 20 mg/kg of heparin was injected into cancer tissues. After lapse of 20 minutes, the ionic-complex nanoparticles of HS-Cy5.5/GC-BHQ3 were injected into veins of the mice tails. Then, decrease of heparanase activities was imaged by using the explore Optix image device.

Figure 4A:
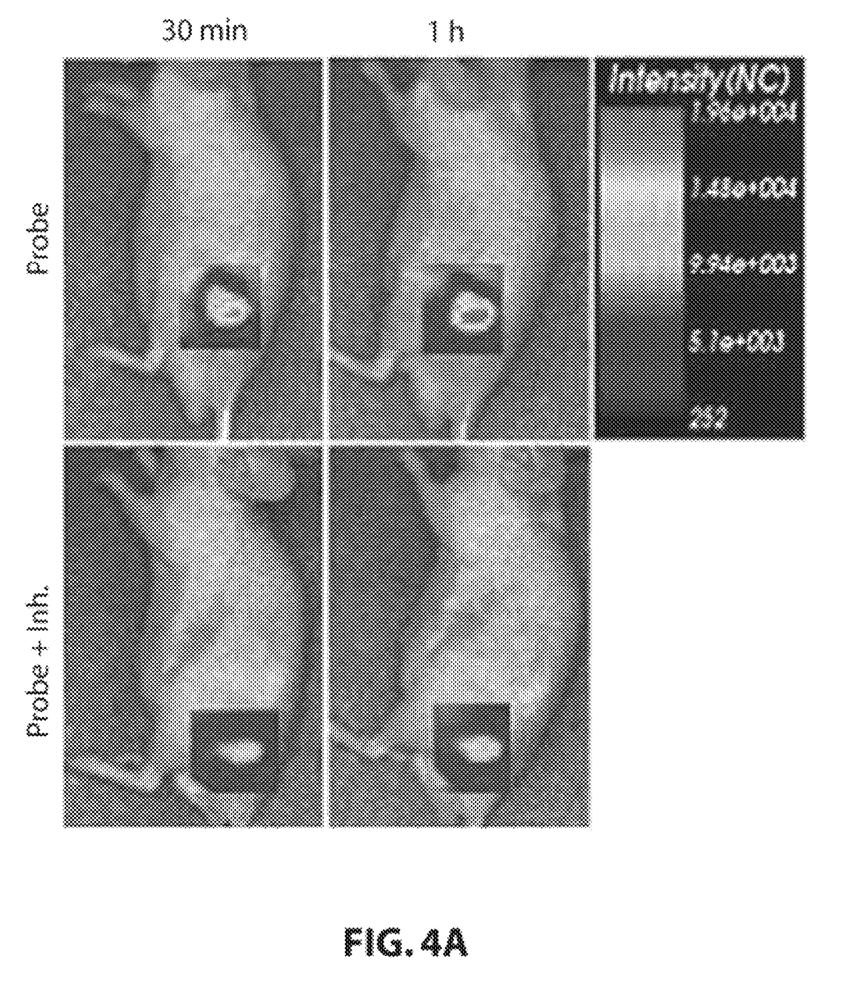
FIG. 4A are images showing, through an optical imaging system, whether heparanase has been expressed after injecting nanoparticles composed of HS-Cy5.5/GC-BHQ3 (probe) to cancer models, and showing whether heparanase activities have been inhibited when the nanoparticles composed of HS-Cy5.5/GC-BHQ3 (probe) were injected to the cancer models after 20 minutes after injecting a heparanase inhibitor thereinto.
Figure 4B:
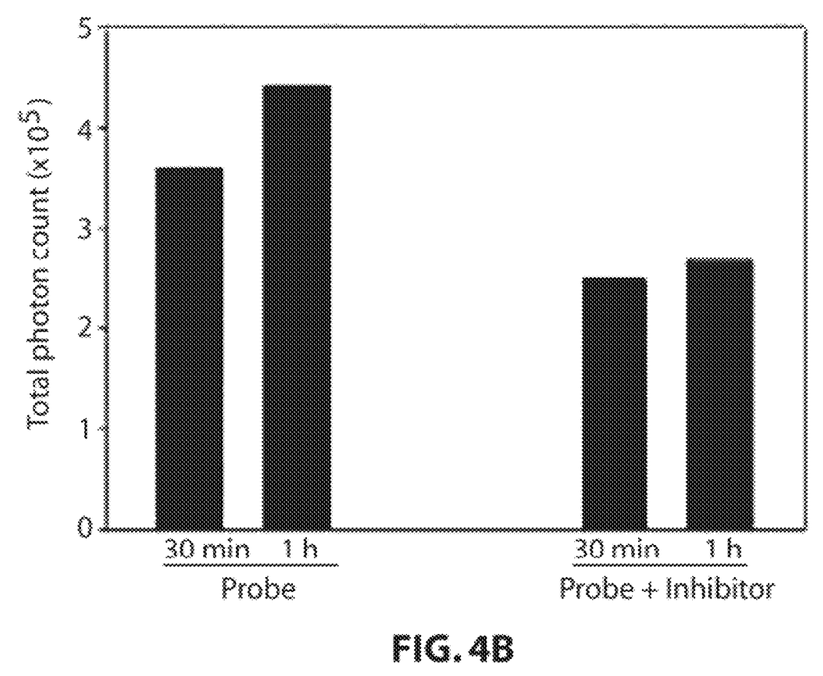
FIG. 4B shows each fluorescence intensity of the two groups of cancer tissues of FIG. 4A in a quantitative manner according to time.
Figure 4C:
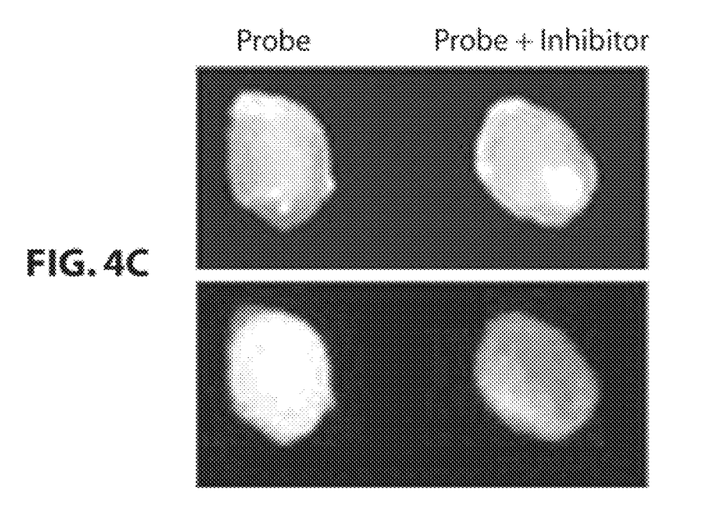
FIG. 4C shows each fluorescence intensity of the two groups of cancer tissues extracted from mice of FIG. 4A, the fluorescence intensity measured by an optical imaging system.

As shown in FIGS. 4A, 4B and 4C, in the case that the ionic-complex nanoparticles of HS-Cy5.5/GC-BHQ3 (probe) were injected into veins of the mice tails, the nanoparticles exhibited a high fluorescence intensity in the cancer tissues. And, a heparanase inhibitor-injected group exhibited a decreased fluorescence intensity. From these experimental results, it could be seen that heparanase expression could be imaged in vivo by using the ionic-complex nanoparticles of HS-Cy5.5/GC-BHQ3 (probe), and efficiencies of the heparanase inhibitor could be measured in vivo.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. An ionic complex nanoparticle for detecting heparanase activity, comprising:
   (a) a negative-ion substrate polymer specifically degraded by heparanase and having a first label covalently conjugated thereto, and
   (b) a positive-ion biocompatible polymer having a second label covalently conjugated thereto,
   wherein:
     one of the first and second labels is a fluorophore and the other label is a fluorescent quencher,
     the negative-ion substrate polymer and the positive-ion biocompatible polymer ionically bind to each other, such that the fluorescent quencher quenches a fluorescent signal emitted by the fluorophore, and exposure of the ionic complex nanoparticle to heparanase reduces quenching of the fluorescent signal.

2. The ionic complex nanoparticle for detecting heparanase activities of claim 1, wherein the nanoparticle is represented by the following chemical formula 1,

[Chemical Formula 1]

wherein 'A' indicates the fluorophe, 'B' indicates the negative-ion substrate polymer specifically degraded by heparanase, 'C' indicates the quencher to implement a quenching effect by absorbing fluorescence emitted from the fluorophore, and 'D' indicates the positive-ion biocompatible polymer that can be specifically accumulated on tissues of cancers and inflammatory disease, and wherein positions of 'A' and 'C' are interchangeable with each other, positions of 'B' and 'D' are interchangeable with each other, the 'B' and 'D' ionically bind to each other, the solid line indicates a covalent bond, and the dotted line indicates an ionic bond.

3. The ionic complex nanoparticle for detecting heparanase activities of claim 1, wherein the fluorophore is selected from a group consisting of fluorescein, BODIPY, Tetramethylrhodamine, Alexa, Cyanine, allopicocyanine fluorophores and derivatives thereof.

4. The ionic complex nanoparticle for detecting heparanase activities of claim 3, wherein the fluorophore is Cyanine or Alexa fluorophores that emit fluorescence of red or infrared rays.

5. The ionic complex nanoparticle for detecting heparanase activities of claim 1, wherein the quencher is selected from a group consisting of blackhole quenchers (BHQ), blackberry quenchers (BBQ), and derivatives thereof.

6. The ionic complex nanoparticle for detecting heparanase activities of claim 3, wherein the quencher is selected from a group consisting of blackhole quenchers (BHQ), blackberry quenchers (BBQ), and derivatives thereof.

7. The ionic complex nanoparticle for detecting heparanase activities of claim 6, wherein the negative-ion substrate polymer specifically degraded by heparanase is selected from a group consisting of heparin sulfate (HS), heparin sulfate proteoglycans (HSPG), heparin, chondroitin-4-sulfate (C4S), chondroitin-6-sulfate (C6S), dermatan sulfate (DS), keratin sulfate (KS) and hyaluronic acid (HA).

8. The ionic complex nanoparticle for detecting heparanase activities of claim 7, wherein the positive-ion biocompatible polymer is the polymer that form the ionic-complex nanoparticle, by an electrostatic attractive force, together with the negative-ion substrate polymer specifically degraded by heparanase, and the positive-ion biocompatible polymer is selected from a group consisting of glycol chitosan, chitosan, poly-L-lysin (PLL), poly beta-amino ester polymer, polyetyleneimine (PEI), poly(amidoamine) (PAMAM) dendrimer and derivatives thereof.

9. The ionic complex nanoparticle for detecting heparanase activities of claim 1, wherein the negative-ion substrate polymer is heparin sulfate (HS), the positive-ion biocompatible polymer is glycol chitosan (GC), the fluorophore is Cyanine fluorophores Cy5.5, and the quencher is blackhole quenchers BHQ-3.

10. The ionic complex nanoparticle for detecting heparanase activities of claim 1, wherein the negative-ion substrate polymer or the positive-ion biocompatible polymer have molecular weight of 2,000-500,000 Da.

11. The ionic complex nanoparticle for detecting heparanase activities of claim 1, wherein 1-30 mol of the fluorophore or the quencher bind to 1 mol of the negative-ion substrate polymer or the positive-ion biocompatible polymer.

12. The ionic complex nanoparticle for detecting heparanase activities of claim 1, wherein the fluorophore bind to the negative-ion substrate polymer, and the quencher bind to the positive-ion biocompatible polymer.

13. The ionic complex nanoparticle for detecting heparanase activities of claim 12, wherein the fluorophores-bound negative-ion substrate polymer and the quenchers-bound positive-ion biocompatible polymer bind each other with a ratio within the range of 1:0.1-1:10.

14. The ionic complex nanoparticle for detecting heparanase activities of claim 12, wherein the ionic-complex nanoparticle has sizes of 50-800 nm.

15. The ionic complex nanoparticle for detecting heparanase activities of claim 12, wherein a distance between the fluorophores and the quenchers in the ionic complex nanoparticles is within 20 nm.

16. A contrast agent composition for imaging heparanase expressed in cells and tissues, the composition comprising the ionic complex nanoparticle as disclosed in claim 1.

17. A composition for a quantitative analysis of heparanase enzymes expressed in cells and tissues, the composition comprising the ionic complex nanoparticle as disclosed in claim 1 as effective components.

18. A composition for screening drugs or effects of drugs, the drugs capable of preventing over-expression of heparanase in cells and tissues, the composition comprising the ionic complex nanoparticle as disclosed in claim 1 as effective components.

19. A method for imaging heparanase for providing information necessary to diagnose cancers, osteoarthritis, rheumatoid arthritis, progressive systemic sclerosis, chronic thyroiditis, ulcerative colitis, or multiple sclerosis by using the ionic complex nanoparticle as disclosed in claim 1.

20. The method for imaging heparanase of claim 19, wherein the cancers are selected from a group consisting of squamous cell carcinoma, uterine carcinoma, uterine cervical cancer, prostatic carcinoma, head and neck cancer, pancreatic carcinoma, brain tumor, breast cancer, liver cancer, skin cancer, esophageal cancer, testicular carcinoma, kidney cancer, large intestine cancer, rectal cancer, stomach cancer, bladder cancer, ovarian cancer, cholangio carcinoma, and gallbladder carcinoma.

21. A method for preparing the ionic complex nanoparticles of claim 1, the method comprising:
    binding fluorophores to negative-ion substrate polymers specifically degraded by heparanase, and binding quenchers to positive-ion biocompatible polymers;
    ionically binding the fluorophores-bound negative-ion substrate polymers, to the quenchers-bound positive-ion biocompatible polymers, thereby forming ionic-complex nanoparticles.

* * * * *